United States Patent
Bergfjord et al.

(10) Patent No.: US 9,878,179 B2
(45) Date of Patent: Jan. 30, 2018

(54) VISION SYSTEM FOR RADIOTHERAPY MACHINE CONTROL

(71) Applicant: Elekta AB (Publ), Stockholm (SE)

(72) Inventors: Per H. Bergfjord, East Grinstead (GB); Daniel Thompson, East Grinstead (GB); Christopher Knox, East Grinstead (GB); Andrew Long, Leatherhead (GB); Stephen Young, Shoreham by Sea (GB)

(73) Assignee: ELEKTA AB (PUBL), Stockholm (SE)

(*) Notice: Subject to any disclaimer, the term of this patent is extended or adjusted under 35 U.S.C. 154(b) by 83 days.

(21) Appl. No.: 15/288,401

(22) Filed: Oct. 7, 2016

(65) Prior Publication Data
US 2017/0036040 A1    Feb. 9, 2017

Related U.S. Application Data

(63) Continuation of application No. 13/458,207, filed on Apr. 27, 2012, now Pat. No. 9,486,647.

(51) Int. Cl.
*A61N 5/10* (2006.01)
*A61B 90/00* (2016.01)

(52) U.S. Cl.
CPC ............ *A61N 5/1048* (2013.01); *A61B 90/36* (2016.02); *A61N 5/1067* (2013.01); *A61N 2005/1059* (2013.01)

(58) Field of Classification Search
CPC .. A61N 5/1042; A61N 5/1048; A61N 5/1049; A61N 2005/1059; A61N 5/1064; A61N 5/1067; G05B 15/02; A61B 90/36
See application file for complete search history.

(56) References Cited

U.S. PATENT DOCUMENTS

| | | |
|---|---|---|
| 5,727,554 A | 3/1998 | Kalend et al. |
| 6,842,502 B2 | 1/2005 | Jaffray et al. |
| 6,853,703 B2 | 2/2005 | Svatos et al. |
| 7,046,765 B2 | 5/2006 | Wong et al. |
| 7,103,144 B2 | 9/2006 | Wong et al. |
| 7,103,145 B2 | 9/2006 | Wong et al. |
| 7,199,382 B2 | 4/2007 | Rigney et al. |
| 7,280,633 B2 | 10/2007 | Cheng et al. |
| 7,446,328 B2 | 11/2008 | Rigney et al. |
| 7,505,559 B2 | 3/2009 | Kuduvalli |

(Continued)

OTHER PUBLICATIONS

Humm, et al., "Collison Detection and Avoidance During Treatment Planning" Int. J. Radiation Oncology Biol. Phys., vol. 33, No. 5, pp. 1101-1108 (1995).

*Primary Examiner* — Charles Kasenge
(74) *Attorney, Agent, or Firm* — Finnegan, Henderson, Farabow, Garrett & Dunner LLP

(57) ABSTRACT

In various embodiments, a system for controlling radiotherapy equipment in a treatment environment includes a controller for receiving, from one or more image capture devices, data indicating the position of one or more objects in the treatment environment. Based on the position data, the controller defines one or more exclusionary zones from which the radiotherapy equipment is excluded. Each zone has a buffer area surrounding one or more of the objects. The controller further directs the radiotherapy equipment such that a radiotherapy treatment plan is delivered without the equipment entering into the exclusionary zones.

20 Claims, 7 Drawing Sheets

(56) References Cited

U.S. PATENT DOCUMENTS

| | | |
|---|---|---|
| 7,746,978 B2 | 6/2010 | Cheng et al. |
| 7,949,096 B2 | 5/2011 | Cheng et al. |
| 7,979,106 B2 | 7/2011 | Kleen et al. |
| 8,002,465 B2 | 8/2011 | Ahn |
| 8,160,205 B2 | 4/2012 | Saracen et al. |
| 8,175,892 B2 | 5/2012 | Kapoor et al. |
| 8,184,773 B2 | 5/2012 | Cheng et al. |
| 8,238,516 B2 | 8/2012 | Sakurai et al. |
| 8,269,195 B2 | 9/2012 | Rigney et al. |
| 8,358,818 B2 | 1/2013 | Miga et al. |
| 8,730,314 B2 | 5/2014 | Hannibal et al. |
| 8,750,453 B2 | 6/2014 | Cheng et al. |
| 9,486,647 B2 * | 11/2016 | Bergfjord ............. A61N 5/1048 |
| 2005/0226377 A1 | 10/2005 | Wong et al. |
| 2005/0281374 A1 | 12/2005 | Cheng et al. |
| 2006/0017022 A1 | 1/2006 | Rigney et al. |
| 2006/0133572 A1 | 6/2006 | Wong et al. |
| 2006/0133573 A1 | 6/2006 | Wong et al. |
| 2007/0041498 A1 | 2/2007 | Olivera et al. |
| 2007/0104316 A1 | 5/2007 | Ruchala et al. |
| 2007/0164230 A1 | 7/2007 | Rigney et al. |
| 2008/0049896 A1 | 2/2008 | Kuduvalli |
| 2008/0187097 A1 | 8/2008 | Cheng et al. |
| 2009/0067577 A1 | 3/2009 | Rigney et al. |
| 2009/0129556 A1 | 5/2009 | Ahn |
| 2009/0175418 A1 | 7/2009 | Sakurai et al. |
| 2009/0187112 A1 | 7/2009 | Meir et al. |
| 2009/0192384 A1 | 7/2009 | Fontius |
| 2010/0292847 A1 | 11/2010 | Cheng et al. |
| 2010/0303205 A1 | 12/2010 | Kapoor et al. |
| 2011/0052036 A1 | 3/2011 | Valdivieso Cacique et al. |
| 2011/0087090 A1 | 4/2011 | Boernert et al. |
| 2011/0135190 A1 | 6/2011 | Maad |
| 2011/0218679 A1 | 9/2011 | Cheng et al. |
| 2011/0249088 A1 | 10/2011 | Hannibal et al. |
| 2011/0286642 A1 | 11/2011 | Nord et al. |
| 2012/0014501 A1 | 1/2012 | Pelc et al. |
| 2012/0043475 A1 | 2/2012 | Ahn |
| 2012/0224667 A1 | 9/2012 | Cheng et al. |
| 2013/0178980 A1 | 7/2013 | Chemouny et al. |

\* cited by examiner

VISION SYSTEM FOR RADIOTHERAPY MACHINE CONTROL

CROSS REFERENCE TO RELATED APPLICATION

This is a continuation of U.S. Application Ser. No. 13/458,207, filed Apr. 27, 2012, which is incorporated herein by reference.

TECHNICAL FIELD

This invention relates generally to methods and systems for the control of radiotherapy equipment, and more specifically to methods and systems for directing the delivery of radiotherapy treatment using a vision control system.

BACKGROUND INFORMATION

Radiation-emitting devices are used for the treatment of cancerous tumors within patients. The primary goal of treating cancerous tumors with radiation therapy is the eradication of the cancerous cells, while the secondary goal is to avoid, to the maximum possible extent, damaging healthy tissue and organs in the vicinity of the tumor. Typically, a radiation therapy device includes a gantry that can be rotated around a horizontal axis of rotation during the delivery of a therapeutic treatment. A particle linear accelerator (LINAC) is located within the gantry, and generates a therapeutic high-energy radiation beam, such as an electron beam or photon (x-ray) beam. The patient is placed on a treatment table located at the isocenter of the gantry, and the radiation beam is directed towards the tumor or lesion to be treated.

Safety is paramount in radiotherapy, and one critical consideration is minimizing or eliminating a collision between the moving parts of the radiotherapy equipment and anything else in the room, be it accessory, operator or patient. During radiotherapy treatment, portions of the equipment or other objects in the treatment environment may be hidden to the operator (who, for safety reasons is in a separate room) as the gantry is rotated around an area of treatment. It is critical that potential collisions be detected prior to their occurrence, such that a radiation treatment plan can be successfully completed despite obstacles in the environment.

Existing systems generally rely on some sort of proximity detector, such as ultrasound, light barrier or a tactile sensor, which requires a moving part to come into a certain proximal range of another object before the system determines that any action is required. These systems, however, are unable to predict whether a collision may occur, and therefore are unable to modify treatment delivery in advance to avoid such collisions and deliver treatment with minimal or no interruption.

Accordingly, a need exists for methods and systems that allow for predictive collision detection for radiotherapy equipment and other objects in a treatment environment that consider treatment delivery plans prior to actual delivery.

SUMMARY OF THE INVENTION

The present invention incorporates a number of image capture devices, such as video cameras, and a vision system controller which is capable of monitoring the position and movement of a patient, the position and movement of radiotherapy equipment, and the positions and movement of any other objects which might potentially be in the path of moving objects in a treatment environment. The controller is able to control the radiotherapy equipment, directing it to change movement speed or direction, stop movement, or, in some cases, terminate treatment altogether if the controller detects that the equipment may enter into an exclusionary zone surrounding an object in the environment and potentially collide with that object.

Accordingly, in general and in one aspect, a system for controlling radiotherapy equipment in a treatment environment includes a connection to one or more image capture devices, and a controller for receiving, from the one or more image capture devices, data indicating a position of one or more objects in the treatment environment. The controller also defines, based at least in part on the received position data, certain exclusionary zones into which movement of the radiotherapy equipment is excluded. Each exclusionary zone comprises a buffer area at least partially surrounding one or more of the objects, and the controller directs the radiotherapy equipment to deliver a radiotherapy treatment plan such that the equipment does not enter into the exclusionary zones.

In one embodiment, the controller also receives, from the one or more image capture devices, data indicating a new position of one of the objects having been moved, wherein the new position indicates that at least a portion of the moved object is outside of the exclusionary zone which previously contained the moved object. In response to the new position data, the controller redefines the exclusionary zone previously containing the moved object such that the redefined zone comprises an updated buffer area surrounding the moved object.

In another embodiment, the controller determines that the redefined exclusionary zone at least partially overlaps with a different exclusionary zone and combines the two or more zones to form a single continuous exclusionary zone, provided that the combination is permissible. In yet another embodiment, the controller determines that two zones are within a threshold distance of each other, and combines the two zones to form a single continuous exclusionary zone, provided that the combination is permissible. The determination of whether the combination is permissible may be based on a visual indicator on an object in one of the zones. Alternatively, the determination may be based on zone combination permissions.

In a further embodiment, the controller further defines a first exclusionary zone having a first buffer area surrounding one or more substantially motionless objects in the treatment environment and defines a second exclusionary zone having a second buffer area surrounding one or more moving objects in the treatment environment. In such cases, the second buffer area may be a surface normal distance greater than the first buffer area.

In some embodiments, each exclusionary zone comprises a buffer area having a non-zero surface normal distance. In yet another embodiment, the controller may determine object motion information based on the received position data, which may include speed, direction, range of motion, and/or frequency of movement.

In certain implementations, the controller defines the exclusionary zones based at least in part on the object motion information. Based on the object motion information, the controller may determine that an object in one of the exclusionary zones has increased in speed and, as a result, redefine the zone or zones to extend the buffer area. The controller may also contract or otherwise reshape the buffer area based on object motion information indicating that an object in one of the exclusionary zones has decreased in speed.

Directing the radiotherapy equipment may include changing the speed of the radiotherapy equipment, changing the direction of the radiotherapy equipment, and/or terminating movement of the radiotherapy equipment.

In some embodiments, the controller may determine the position of each image capture device based at least in part on a visual indicator in a field of view of the device. The system may also include a connection to an image projection device, and in such cases the controller may transmit a visual indicator of an action to be taken with respect to an object in the treatment environment to the image projection device for projection onto a surface in the treatment environment.

The controller may also activate an alert device based on the received position data. The alert device may include one or more colored lights on certain portions of the radiotherapy equipment, and activating the alert device may include changing the state of the lights based on a component of the radiotherapy equipment being in proximity to or moving in the direction of another object in the treatment environment. In certain cases, the alert device includes an auditory signal, and activating the alert device includes varying the signal based on a proximity of a first object in the treatment environment to a second object in the treatment environment.

In some embodiments, the controller determines whether a collision is likely to occur during delivery of the plan. Such a determination may be made prior to directing delivery of the radiotherapy treatment plan, and be based at least in part on the received position data and the radiotherapy treatment plan. The controller may repeatedly receive the position data and define the exclusionary zones substantially contemporaneously with directing delivery of the radiotherapy treatment plan.

In another aspect, a method for controlling radiotherapy equipment in a treatment environment includes receiving, from one or more image capture devices, data indicating a position of one or more objects in the treatment environment and defining, based at least in part on the position data, one or more exclusionary zones from which the radiotherapy equipment is excluded. Each zone includes a buffer area at least partially surrounding one or more of the objects, and the radiotherapy equipment is directed to deliver a radiotherapy treatment plan such that the equipment does not enter into the exclusionary zones.

The method may, in some cases, include receiving, from the image capture devices, data indicating a new position of a moved object such that at least a portion of the moved object is outside of the exclusionary zone that previously contained the moved object. In response to the new position data, the exclusionary zone previously containing the moved object may be redefined such that the redefined zone comprises a buffer area surrounding the moved object.

In some embodiments, the method further includes determining that the redefined exclusionary zone at least partially overlaps with a different one of the exclusionary zones and combining the redefined zone and the different zone to form a single continuous exclusionary zone, provided that the combination is permissible. In another embodiment, the controller determines that two zones are within a threshold distance of each other, and combines the two zones to form a single continuous exclusionary zone, provided that the combination is permissible. The determination of whether the combination is permissible may be based on a visual indicator on an object in one of the zones. Alternatively, the determination may be based on zone combination permissions.

In a further implementation, the method may include defining a first exclusionary zone having a first buffer area surrounding one or more substantially motionless objects in the treatment environment and defining a second exclusionary zone having a second buffer area surrounding one or more moving objects in the treatment environment. In such cases, the second buffer area may comprise a surface normal distance greater than the first buffer area.

In some embodiments, the exclusionary zones each may comprise a buffer area having a non-zero surface normal distance. In yet another embodiment, the method further includes determining object motion information based on the received position data, which may include speed, direction, range of motion, and/or frequency of movement of the radiotherapy device, components of the device, other objects in the treatment room, and/or elements of the treatment room itself (walls, ceiling, etc.).

In some implementations, the definition of the exclusionary zones based at least in part on the object motion information. In a further embodiment, the definition of the zones may be expanded (or contracted) based on detecting that the movement of an object in one of the zones has increased (or decreased) in speed.

Directing the radiotherapy equipment may include changing a speed of the radiotherapy equipment, changing a direction of the radiotherapy equipment, and/or terminating movement or, in some cases, use of the radiotherapy equipment.

In some embodiments, the position of each image capture device is determined based at least in part on a visual indicator in a field of view of the device. In such cases, a visual indicator of an action to be taken with respect to an object in the treatment environment may be transmitted to an image projection device for projection onto a surface in the treatment environment.

In some cases, an alert device is provided, and activated based at least in part on the received position data. The alert device may include colored lights placed on a portion of the radiotherapy equipment, and activating the alert device may comprise changing the state of the lights based on a proximity of the portion of the radiotherapy equipment to another object in the treatment environment. In other embodiments, the alert device includes an auditory signal, and activating the alert device includes varying the signal based on a proximity of a first object in the treatment environment to a second object in the treatment environment.

In some implementations, the method may include determining whether a collision is likely to occur during delivery of the plan. Such a determination may be made prior to directing delivery of the radiotherapy treatment plan, and be based at least in part on the received position data and the radiotherapy treatment plan itself. The position data may, in some cases, be received repeatedly and the exclusionary zones defined substantially contemporaneously with receipt of the position data, thus directing delivery of the radiotherapy treatment plan with a defined periodicity driven, at least partially, by the receipt of the position data.

Other aspects and advantages of the invention will become apparent from the following drawings, detailed description, and claims, all of which illustrate the principles of the invention, by way of example only.

BRIEF DESCRIPTION OF THE DRAWINGS

A more complete appreciation of the invention and many attendant advantages thereof will be readily obtained as the same becomes better understood by reference to the following detailed description when considered in connection with the accompanying drawings. In the drawings, like reference characters generally refer to the same parts throughout the different views. Further, the drawings are not necessarily to scale, emphasis instead generally being placed upon illustrating the principles of the invention.

DETAILED DESCRIPTION

Figure 1:
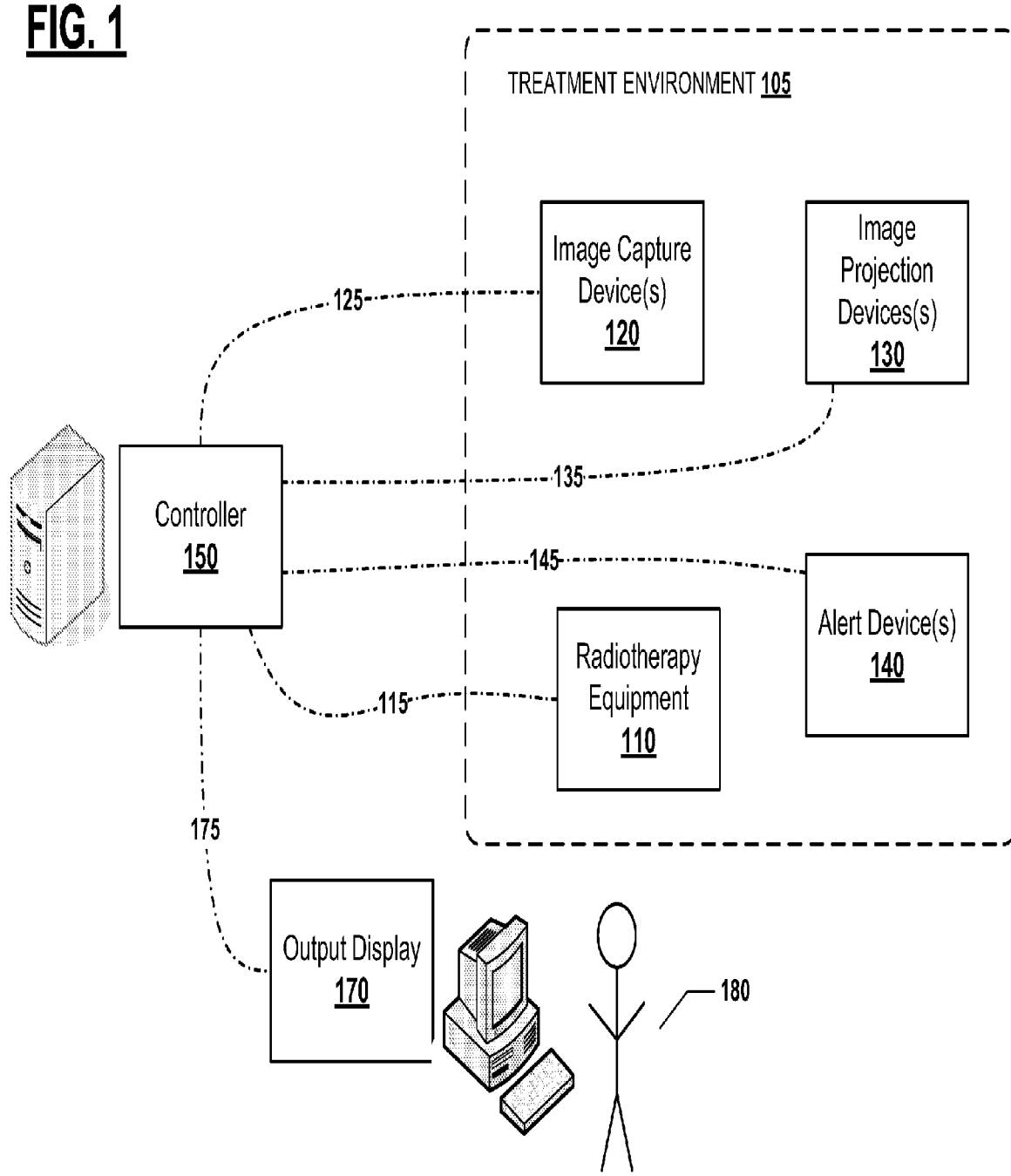
FIG. 1 is a diagram illustrating by example various features and embodiments of the invention.

Referring to FIG. 1, an example of a system in accordance with various embodiments of the invention is shown. A treatment environment 105 includes radiotherapy equipment 110 and one or more image capture devices 120. The treatment environment 105 may also include one or more image projection devices 130 and alert devices 140. A controller 150 connects to the various objects in the treatment environment 105, including a connection 115 to the radiotherapy equipment 110 and a connection 125 to the image capture devices 120. The controller 150 may further have a connection 135 to the image projection devices 130 and a connection 145 to the alert devices 140. In some embodiments, the controller 150 has a connection 175 to an output display 170. The connections may be of any sort, including, for example, wired or wireless networks and/or dedicated communication lines. The display 170 may provide information about the operation of the radiotherapy equipment 110 or other devices in the treatment environment 105 to an operator 180, observer, patient, or other personnel. The display 170 may also be connected to the image capture devices 120 so that the operator can observe the operation of the radiotherapy equipment 110. The operator 180 may also have access to a control panel (not shown) to manually operate the equipment 110. In some cases, the controller 150 and/or the display 170 may be physically remote from the treatment environment 105 to allow the operator 180 to remain a safe distance from the radiotherapy equipment 110, and, in some cases, to operate the devices from remote locations.

Figure 2:
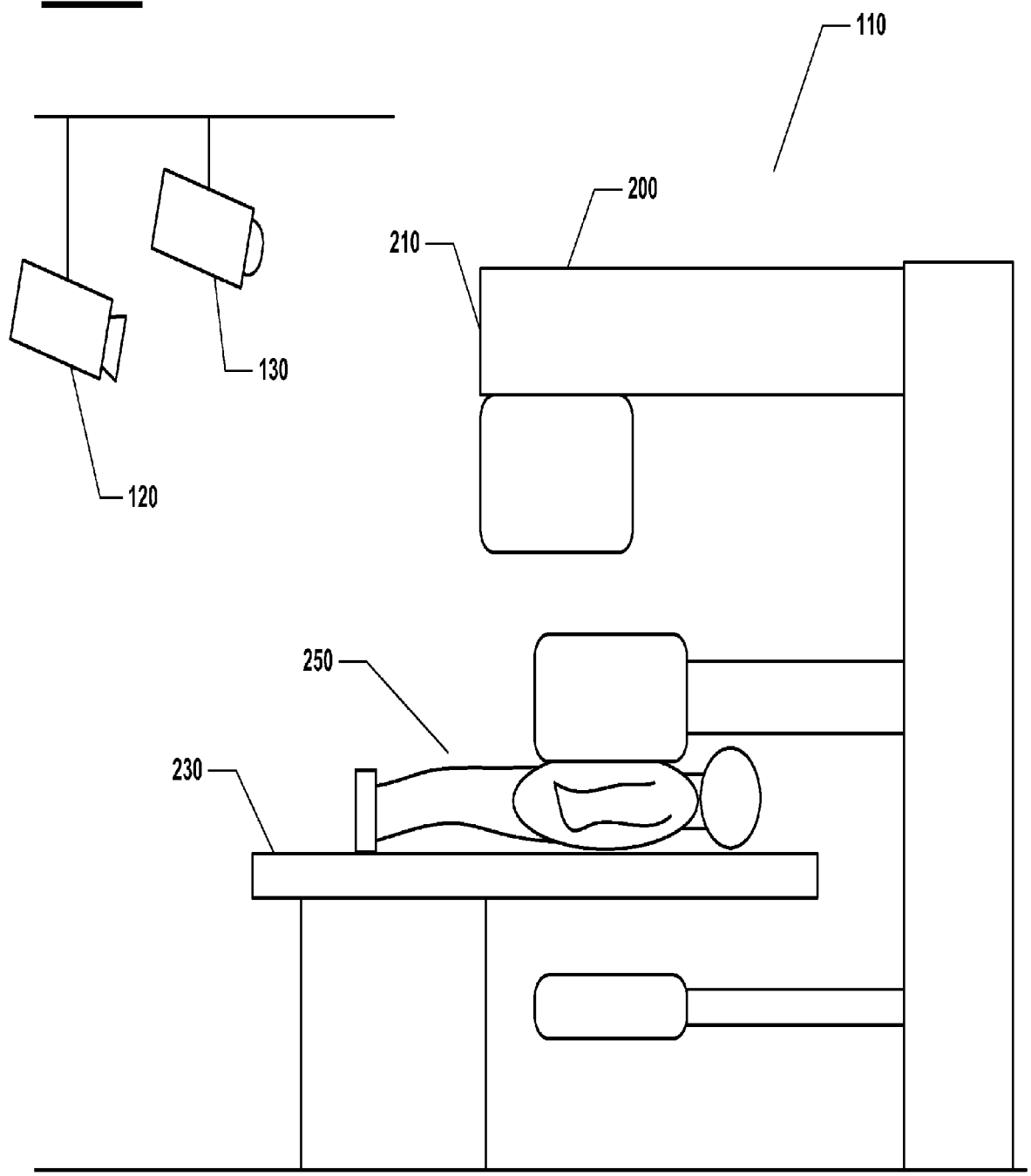
FIG. 2 is an illustration of an exemplary treatment environment in accordance with an embodiment of the invention.

Exemplary radiotherapy equipment is illustrated in FIG. 2. A linear accelerator (LINAC) 200 is used to generate and deliver a radiation beam to a patient 250 supported on couch 230. Typically, the beam is generated by a radiation source contained within the LINAC head 210. A target volume, to which the beam is to be administered, has previously been identified and defined in or on the patient's body. The volume may, for example, be a cancerous tumor which is to be treated by introducing the biological effects of the radiation beam to the target according to a radiation treatment and dosage plan. Although radiotherapy equipment with a LINAC is described herein for purposes of illustrating the disclosed embodiments, one skilled in the art will appreciate that the present invention may used in conjunction with any type of medical equipment in which a risk of collision exists, including radiotherapy and radiosurgery machines, MRI, CT/PET scanners, ultrasound devices, x-ray devices, and other devices that incorporate a moveable linear accelerator or other imager.

The treatment environment 105 includes one or more image capture devices 120. One example of a suitable device for a collision avoidance system is a standard commercial off-the-shelf video camera, although other devices may be used, such as digital still-image cameras, digital video cameras, webcams, 3-D cameras, and closed-circuit television cameras. In some embodiments, the image capture devices are able to detect invisible portions of the electromagnetic spectrum, e.g., infrared or ultraviolet. The devices 120 may all be of the same type, or may include a combination of different types of devices. Any suitable means of image capture may be used, provided the resulting images have sufficient quality to allow for image processing and analysis in accomplishing the goals of the present invention. Those skilled in the art will recognize the minimum requirements of an image capture device such that it would be usable in the disclosed collision avoidance system.

The image capture devices 120 may be placed at various positions and angles within the treatment environment 105 so as to provide a complete view of the radiotherapy equipment 110 and/or other objects that may be in the path of the equipment 110, such as the patient 250, as well as the room itself. In some embodiments, the image capture devices 120 may be directed only toward a portion of the equipment or object(s) of interest in the environment 105. Each device 120 may have a field of view that encompasses a different portion of the environment 105, or same or similar portions of the environment, but at different angles. The fields of view of the devices 120 may be separate or may overlap. For example, a first image capture device 120 may be positioned such that its field of view includes the length of the patient 250 along the sagittal plane, and a second device 120 may view the patient 250 along the transverse plane. If there are multiple image capture devices 120, they may be positioned so as to allow the controller 150 to evaluate the movement, in three-dimensional space, of objects in the treatment environment 105.

The treatment environment 105 may include various forms of lighting to allow objects in the room 105 to be more readily identified by the controller 150. For example, backlighting may be used to avoid issues with skin contrast. The use of backlighting in the room 105 can further be used to overcome the problem of objects being camouflaged within the background of images captured by the cameras 120, and to provide an indication to an operator of which camera is being used to provide the video image(s).

In some embodiments, visual indicators are provided in the treatment room 105 so that the controller 150 or an operator 180 can determine the position and/or angle of each image capture device 120. For instance, each wall of the room 105 may be differently colored (e.g., by projecting colored lights), or may have text, a symbol, or other graphical indicator corresponding to a particular field of view. In one example, using colored walls, a "blue view", "red view", and "yellow view" could correspond to cameras displaying east, west, and cranial-caudal views.

Once positioned, the image capture devices 120 provide image data to the controller 150, which allows the controller 150 to monitor the position and/or movement of the patient and/or other persons in the treatment environment 105, the position and/or movement of the radiotherapy equipment, and the positions and/or movement of any other objects which might potentially be in the path of the moving objects.

The controller 150 is able to direct the operation of the radiotherapy equipment 110 through a connection 115. For example, the controller 150 may direct the equipment 110 to deliver a predefined radiotherapy treatment plan stored in a memory device or register (not shown). In response to data received from devices in the treatment environment 105 (e.g., the image capture devices 120), the controller 150 may either deliver radiotherapy according to the plan, or, in some cases modify the plan (e.g., by altering the movement of the equipment 110) to avoid or minimize potential collisions between the radiotherapy equipment 110 and other objects in the environment 105. The controller may alter the manner of delivery prior to commencing treatment, or it may do so in substantially real-time while treatment is occurring, such that the intended treatment plan can be delivered with little or no interruption. For example, the controller 150 may direct the equipment 110 to change speed or direction, or may stop the equipment 110 from moving (and, in some cases, delivering radiotherapy altogether) if a collision is otherwise unavoidable. The controller may receive data from devices in the treatment environment 105 one or more times, at fixed or varied intervals, or continuously.

In some embodiments, the controller 150 analyzes object position data from the image capture devices 120 prior to the start of treatment. Using this position data in conjunction with knowledge of the planned machine movements during treatment, the controller then determines if anything in the treatment environment 105 is in danger of a collision during the course of treatment. This analysis may be performed before the equipment operator 180 leaves the room 105, allowing the operator 180 to make modifications to the position of the patient 250 or other objects in the room 105. In this regard, the system saves valuable time for the operator 180 because he will not have to stop treatment and return to the room 105 to remedy potential or actual collisions.

To efficiently monitor for potential collisions between objects in the treatment environment 105, the controller 150 defines exclusionary zones around one or more of the objects. By defining zones around objects in the treatment room 105, rather than tracking the object surfaces themselves, it is not necessary to engage in motion tracking or capture, which can require substantial processing and/or complex equipment. Instead, objects are allowed a range of movement within their exclusionary zones, and the controller 150 need not take action with respect to the zones or delivery of a treatment plan unless and until an object moves outside of its zone. In essence, the system permits free movement of any object within the environment unless it appears as if such movement will lead to a collision.

Using position data received from the image capture devices 120, the controller 150 may set zones entirely or partially surrounding the patient 250, medical personnel, portions of the radiotherapy equipment 110, furniture, and/or other objects in the environment 105. A number of parameters may be used in the computation of the exclusionary zones, including but not limited to: the size and dimensions of the surrounded object(s), the expected movements of the object(s) during treatment, and the locations of the object(s). Each exclusionary zone may contain a buffer area between the surface of the surrounded object and the zone boundary; for example, a suitable buffer area may have a surface normal distance ranging from, e.g., 0.5 cm to 1 m, although any distance appropriate for the circumstances may be used, including a zero distance (i.e., the boundary of the exclusionary zone is coincident with the surface of the encompassed object(s)). In the present disclosure, "surface normal distance" refers to the length of the normal extending from the outer surface of the surround object and terminating at the zone boundary.

In some embodiments, overlapping exclusionary zones are combined to reduce duplicative processing and analysis. In other embodiments, the controller 150 creates a single, continuous exclusionary zone to encompass objects that are within a certain distance of each other (e.g., 1 cm, 20 cm, 0.5 m, 1 m) or that are substantially in contact. For example, when adding an electron applicator to the bottom of the LINAC head 210, the exclusionary zones of the two components may be combined to form a single zone around both. In other circumstances, however, it may not be preferable to combine zones that overlap or are within a threshold distance of each other. For example, combining an exclusionary zone encompassing the patient 250 with an exclusionary zone surrounding the moving LINAC head 210 would defeat the purpose of collision avoidance. Therefore, the controller 150 may make a determination as to whether one exclusionary zone should be combined with another.

The controller 150 may use image data from the image capture devices 120; e.g., recognition of visual indicator(s) on objects in the treatment environment 105. These indicators may be, for example, markers on the radiotherapy equipment 110 indicating that the exclusionary zone surrounding the equipment 110 should not be combined with other zones. In other cases, there may be multiple types of markers or symbols on various objects, each symbol representing which exclusionary zones may or may not be combined with the zones surrounding the objects. The controller 150 may also be programmed to recognized certain shapes, colors, text, objects, or other visual data to make a determination on zone combination. For example, the controller 150 may recognize the general shape of the patient 250, and allow combination of the patient's 250 zone only with certain other zones (such as the couch 230), or no zone at all. The controller 150 may also be aware of the layout of the environment 105 and the objects within, and may utilize this knowledge in making combination decisions.

In further embodiments, the controller 150 has access to information specifying permissible zone combinations. The controller 150 may then recognize objects using image data from the cameras 120, and refer to the zone combination permissions to determine whether to combine two or more zones. In one example, the permission information may specify that zones encompassing the patient 250 may be combined with zones surrounding patient supports, but may not be combined with zones surrounding moving components of the radiotherapy equipment 110. In another example, the permission information may indicate that newly recognized objects may not have their zones combined with any other zone. The permission information may contain logic based on object type, shape, size, color, speed, direction, and other object characteristics, as well as time-based logic, such as time since last object movement, time since treatment delivery commencement, frequency of movement, and so on.

The exclusionary zones may be defined as substantially planar sheets encompassing one or more objects, or may be contoured to the surfaces of the surrounded objects. The surface normal distance of a zone buffer area may vary based on various factors; for example, a larger buffer area may be placed around objects that are more likely to move or are more susceptible to radiation, such as the patient 250. Conversely, a smaller buffer area may be placed around an object that is known to be motionless, such as a cabinet affixed to a wall. Recognition of these objects may be preprogrammed into the controller 150, or may be determined via imaging data received from the image capture devices 120 (e.g., by a visual marker, coloring, detected movement, or other indicator).

Buffer areas may also be dynamically increased and/or decreased during treatment delivery. For instance, if the controller 150 determines that an object has increased in speed, it may increase the buffer area surrounding that object. In addition, or alternatively, the controller 150 may increase the buffer area surrounding objects that are in close proximity to the faster moving object. Likewise, a decrease in speed may result in a reduction of the aforementioned buffer areas. Buffer size may also be determined based on the frequency with which an object moves, or on its known or detected range of motion. For example, the controller 150 may define a zone with a larger buffer area around a patient's chest based on a preprogrammed assumption or on frequency of movement data derived from imaging data from the image capture devices 120. In other words, because the patient will be breathing during treatment delivery, a slightly larger exclusionary zone is defined to account for chest movement.

Figure 3:
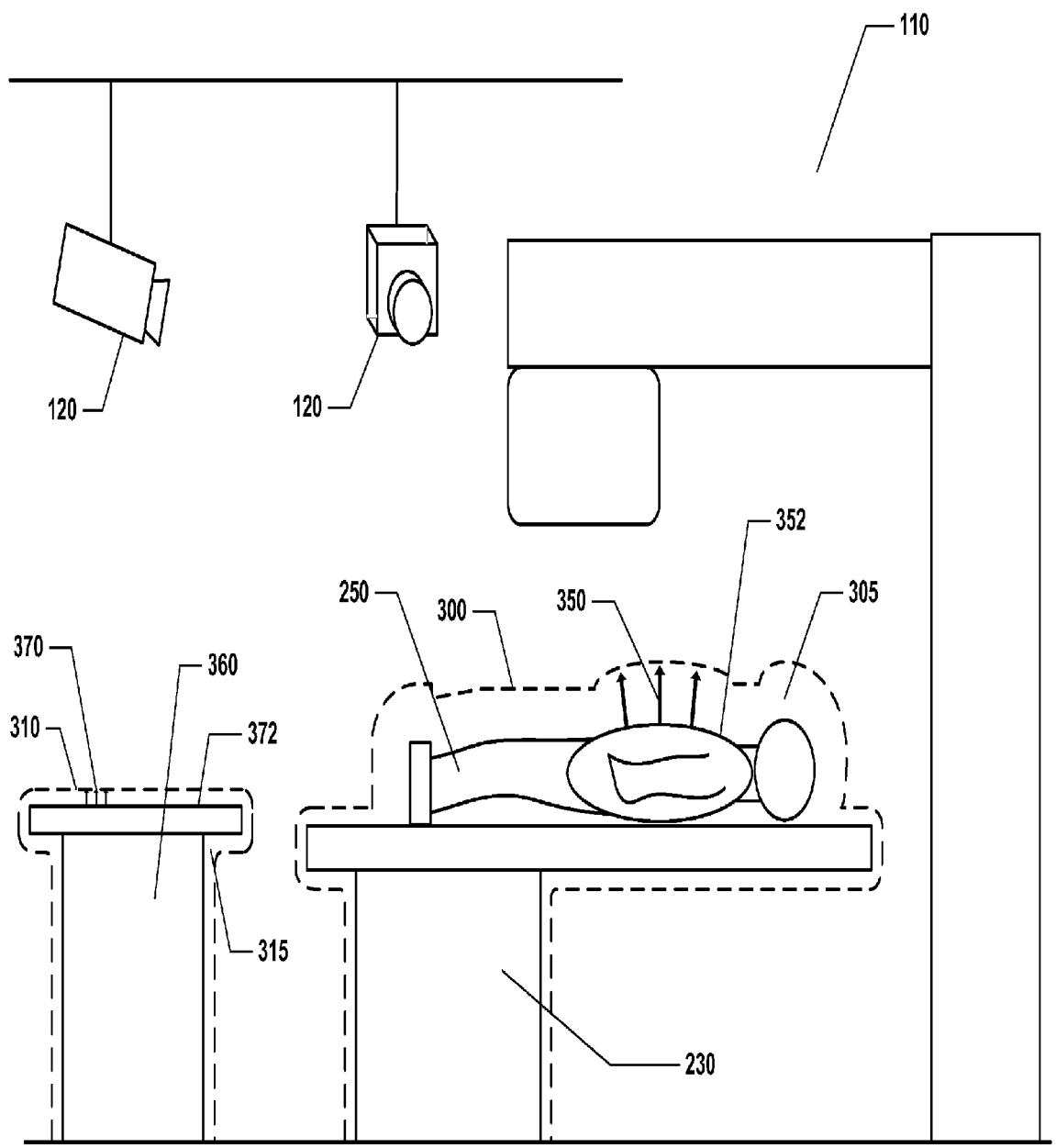
FIG. 3 is an illustration of an exemplary treatment environment including exclusionary zones in accordance with an embodiment of the invention.

Referring now to FIG. 3, the controller 150 has defined a first exclusionary zone 300 around the patient 250 and the couch 230, and a second exclusionary zone 310 around a table 360 in the treatment environment 105. The first zone 300 has a buffer area 305 between the surface 352 of the patient and the boundary of the zone 300. The surface normal distance 350 for the buffer area 305 is large enough to allow some movement of the patient 250 within the zone 300 (e.g., 20 cm). The second zone 310 has a buffer area 315 with a smaller surface normal distance 370 (e.g., 5 cm) than the buffer area 305 for the first zone 300. In this case, the table 360 is known to be fixed to the floor and substantially motionless; therefore, the controller 150 allows for a smaller exclusionary zone around the table 360 because it is less likely that the table 360 will move and enter into a path of potential collision with another object in the room.

Figure 4:
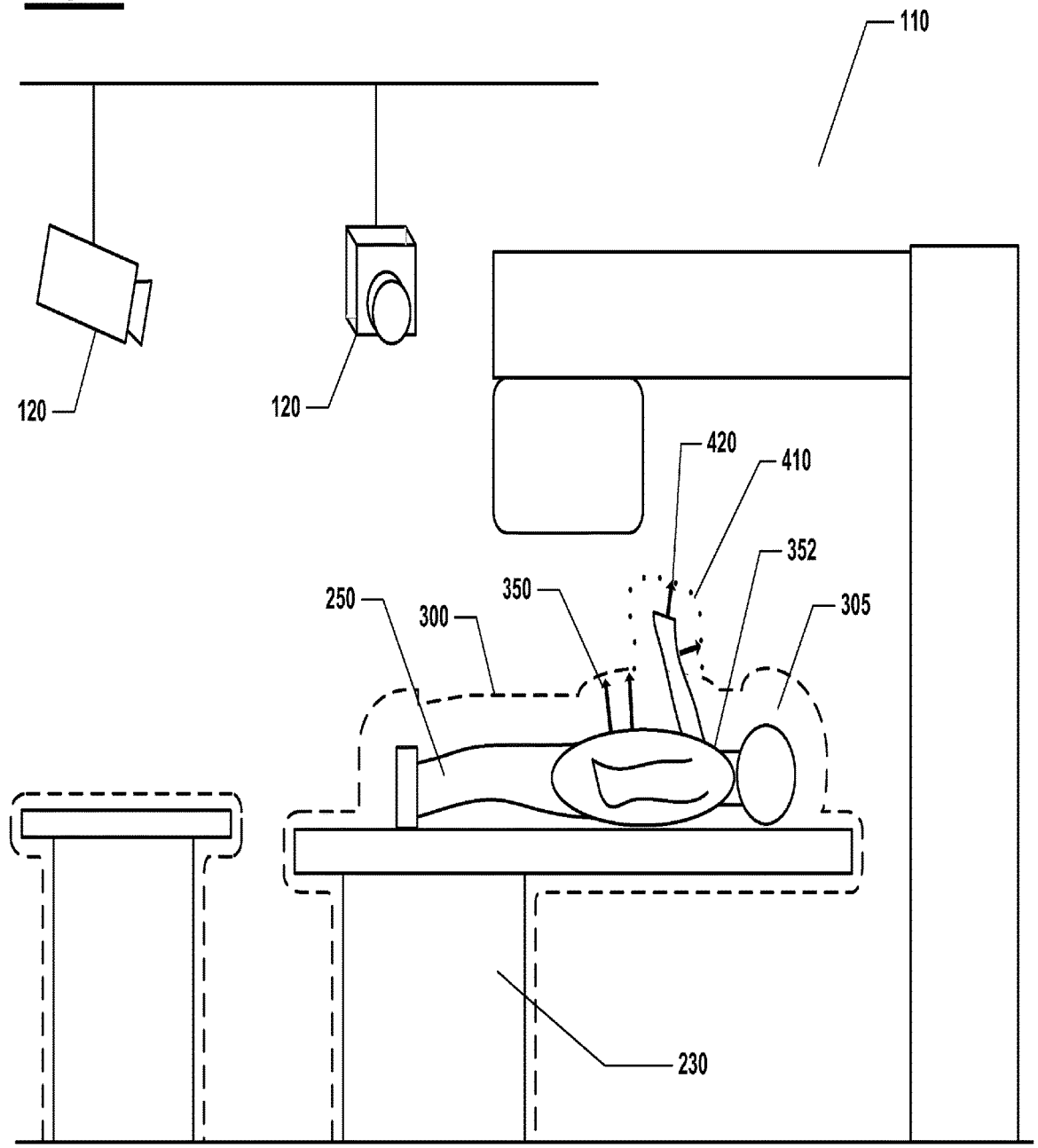
FIG. 4 is an illustration of an exemplary treatment environment including a redefined exclusionary zone in accordance with an embodiment of the invention.

Upon detecting movement of an object outside of its surrounding zone, the controller 150 may redefine the zone to fully encompass the object. The controller 150 may further direct the radiotherapy equipment 110 to begin or continue treatment delivery without the equipment 110 entering into the redefined zone. In some circumstances, if a collision is unavoidable even with the redefined zone, the controller 150 may halt operation of the equipment 110. As shown in FIG. 4, the patient 250 has extended his arm outside of exclusionary zone 300. One or more of the image capture devices 120 detect this movement, and provide position data to the controller 150. Using this data, the controller 150 redefines the zone 300 so that it includes a new zone portion 410 encompassing the arm of the patient 250. The buffer area of the new zone portion 410 may have the same or different surface normal distance than the portion of the zone 300 surrounding the rest of the patient 250. For example, the controller 150 may set a larger normal distance 420 for the new zone portion 410 because of an assumption that further movement will occur around the area of the patient's extended arm.

In some embodiments, the controller 150 will also redefine an exclusionary zone upon detecting that an object in the zone has moved closer to the border of the zone, even though the object has not breached the zone boundary. For example, the controller 150 may receive image data, over a period of time, from the image capture devices 120 indicating that the patient's legs frequently move and approach the edge of the zone surrounding the patient. The controller 150 may then enlarge that zone such that the patient will be less likely to cross the zone boundary during treatment delivery.

Figure 5:
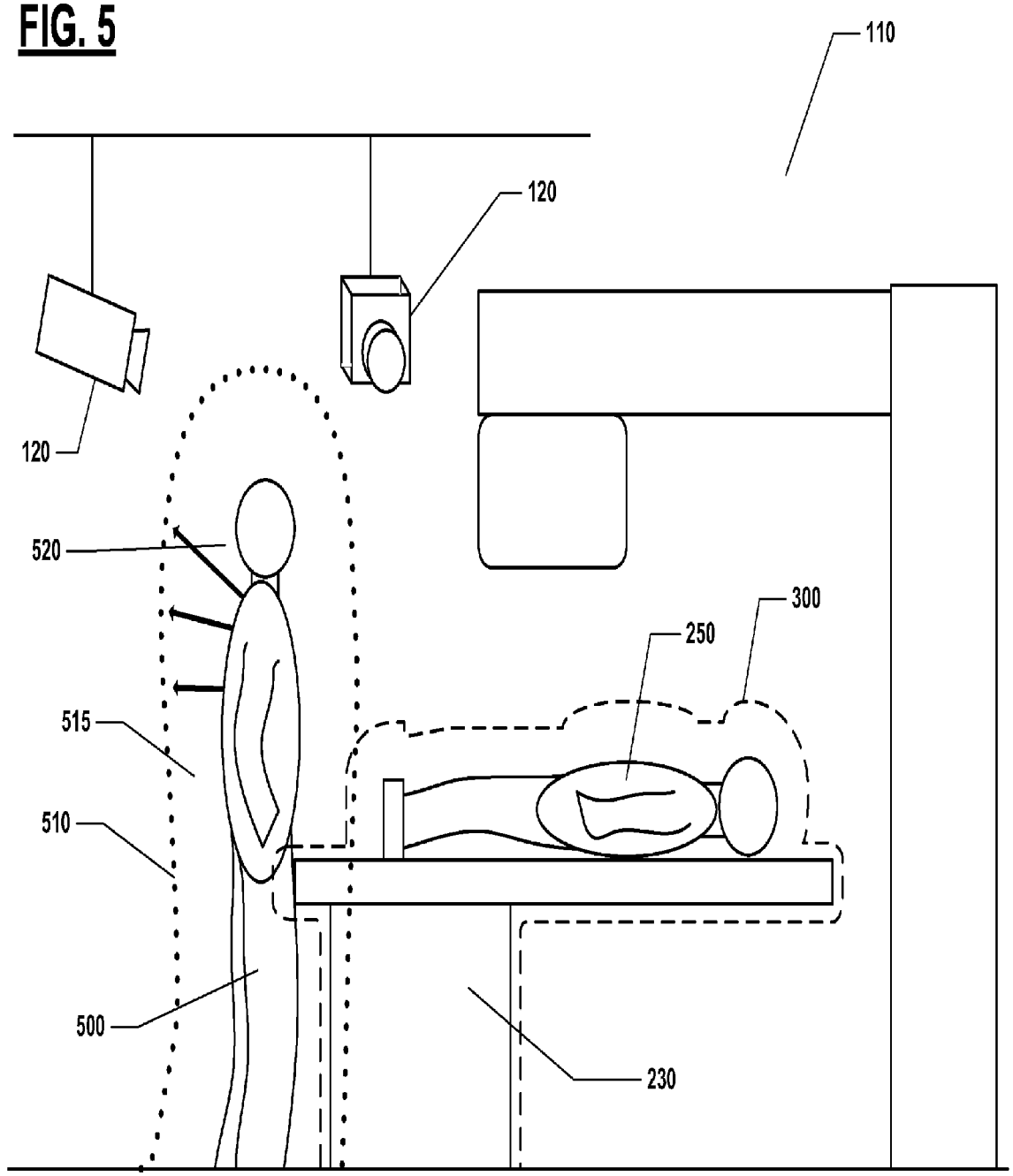
FIG. 5 is an illustration of an exemplary treatment environment including a newly added exclusionary zone in accordance with an embodiment of the invention.
Figure 6:
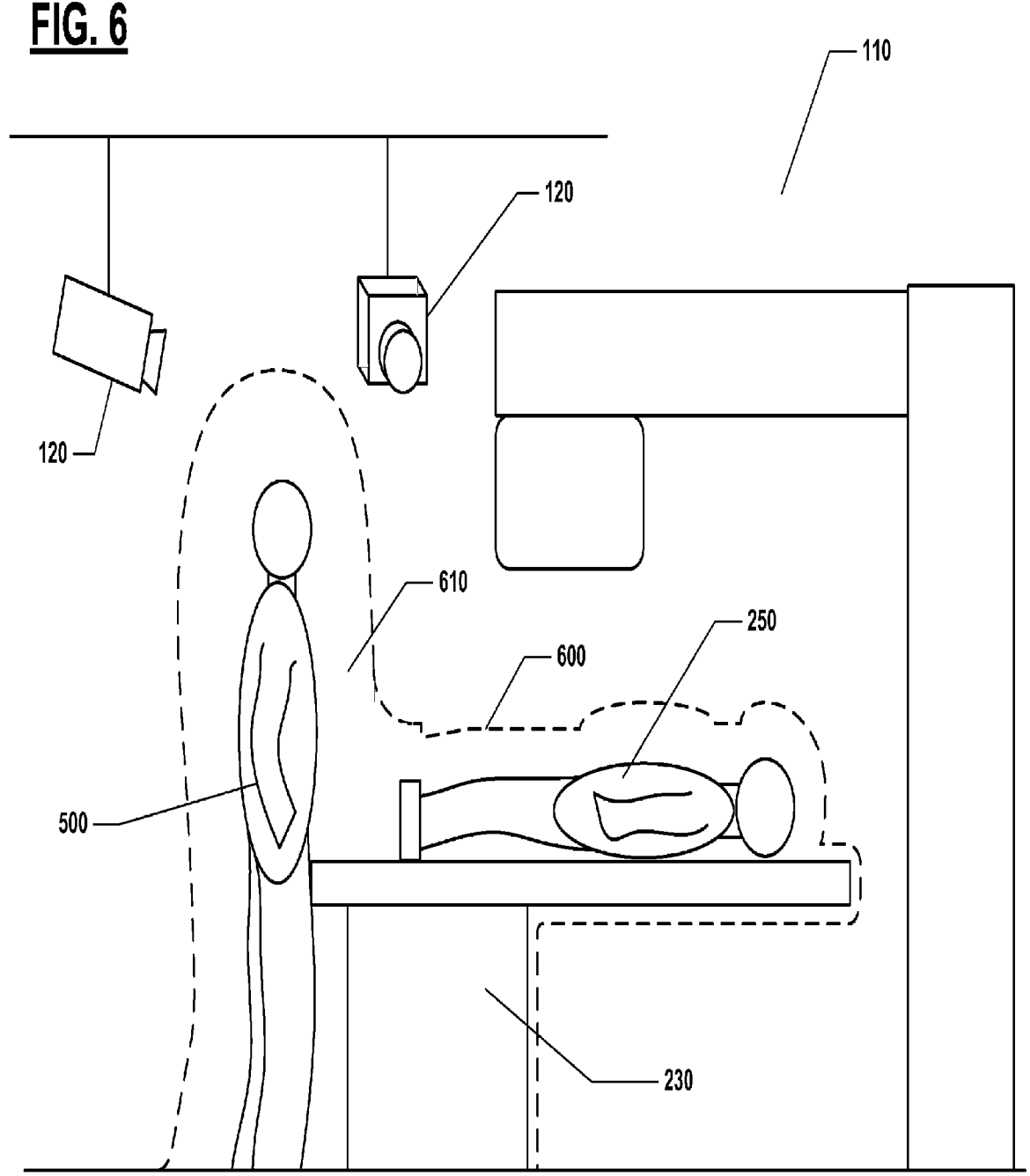
FIG. 6 is an illustration of an exemplary treatment environment including a combined exclusionary zone in accordance with an embodiment of the invention.

The controller 150 may define exclusionary zones around new objects entering the treatment environment 105 before or during treatment delivery, such that the new objects will be automatically considered when moving the radiotherapy device. For example, referring to FIG. 5, a physician 500 entering the treatment room 105 is surrounded by a newly defined exclusionary zone 510. The zone 510 has a buffer area 515 with a normal distance 520 between the surface of the physician 500 and the boundary of the zone 510. The normal distance 520 may be large (e.g., 0.5 m) to accommodate movement of the physician 500. In some embodiments, the controller 150 may combine new exclusionary zones with existing exclusionary zones if they overlap. Referring to FIG. 6, the exclusionary zone 510 surrounding the physician 500 and the exclusionary zone 300 surrounding the patient 250 and the couch 230 have been combined into a single, continuous exclusionary zone 600. The buffer area 610 may include a constant or varying normal distance between the zone boundary and surrounded objects.

In certain implementations, embodiments of the present invention feature a controller 150 for detecting, and responding to, the relative passage of the radiotherapy equipment 110 into one or more exclusionary zones. The exclusionary zones are fixed relative to, and surround (at least in part) the patient 250 or other objects in the treatment environment 105. In other versions, an exclusionary zone is fixed with respect to, and travels with, the moving portion(s) of the radiotherapy equipment 110. In this form, the controller 150 detects and responds to the relative passage of any object (e.g., the patient or equipment or any other object) into the exclusionary zone. In each case, the controller 150 prevents collision of any moving equipment with another object in the treatment environment 105.

In a manually controlled system, the controller 150 is responsive to a user action, taken in response to observation of an object extending within an exclusionary zone, to interrupt any further motion of radiotherapy equipment 110 toward the exclusionary zone. In other words, the user may press a switch or a button as soon as the user observes any object extending within the exclusionary zone. In response, the controller 150 directs the equipment 110 to interrupt any further movement toward the exclusionary zone. Alternatively, the system may be automatically activated such that an object extending toward or within an exclusionary zone automatically triggers the controller 150 to direct the radiotherapy equipment 110 to change speed or direction, or terminate movement entirely.

The controller 150 may send signals to one or more image projection devices 130. The projection devices 130 may be any of suitable form, such as an LCD projector, CRT projector, LED projector or any other type of digital or analog projection device suitable for use in the present invention. In some embodiments, the devices 130 project different colored lights on surfaces of the treatment environment 105 so that the positions of the image capture devices 120 can be identified. In other embodiments, at least one of the projection devices 130 is aligned to point towards the patient and the machine, and to project output onto a surface in the view of one or more of the image capture devices 120. The projection device 130 may project symbols, colors, or other images onto the radiotherapy equipment 110, the patient 250, or other surface in the treatment environment 105. For example, the projector 130 may project an image of an arrow indicating that the equipment 110, patient 250, or other object needs to be moved. In another example, the projector 130 may project a range of colors onto various objects in the room 105 depending on how close the object is to a potential collision (e.g., yellow when nearing collision, red when collision is imminent).

The projection device(s) 130 may be active before or during treatment delivery. As described above, the controller 150 may use data from the image capture devices 120 to determine if a collision is in danger of occurring prior to starting treatment. Subsequently, the controller 150 may determine that a particular object (e.g., a catheter stand) is placed incorrectly, and/or is in the movement path of the radiotherapy equipment 110, and may cause a projection device 130 to project a visual warning indicator onto the stand, an object near the stand, on a wall, or other surface in the treatment environment 105. The indicator may take various forms. In one example, the indicator is an arrow projected on or near the catheter stand indicating a direction in which the stand should be moved. In another example, the projection device 130 projects an indicator on the floor or other surface representing an area where the stand should be relocated to. In other circumstances, the projection device 130 may project a symbol or textual explanation on the wall or other surface describing the problem to the operator 180 or other personnel. The symbol or description may include a suggestion on how to resolve the problem.

Figure 7:
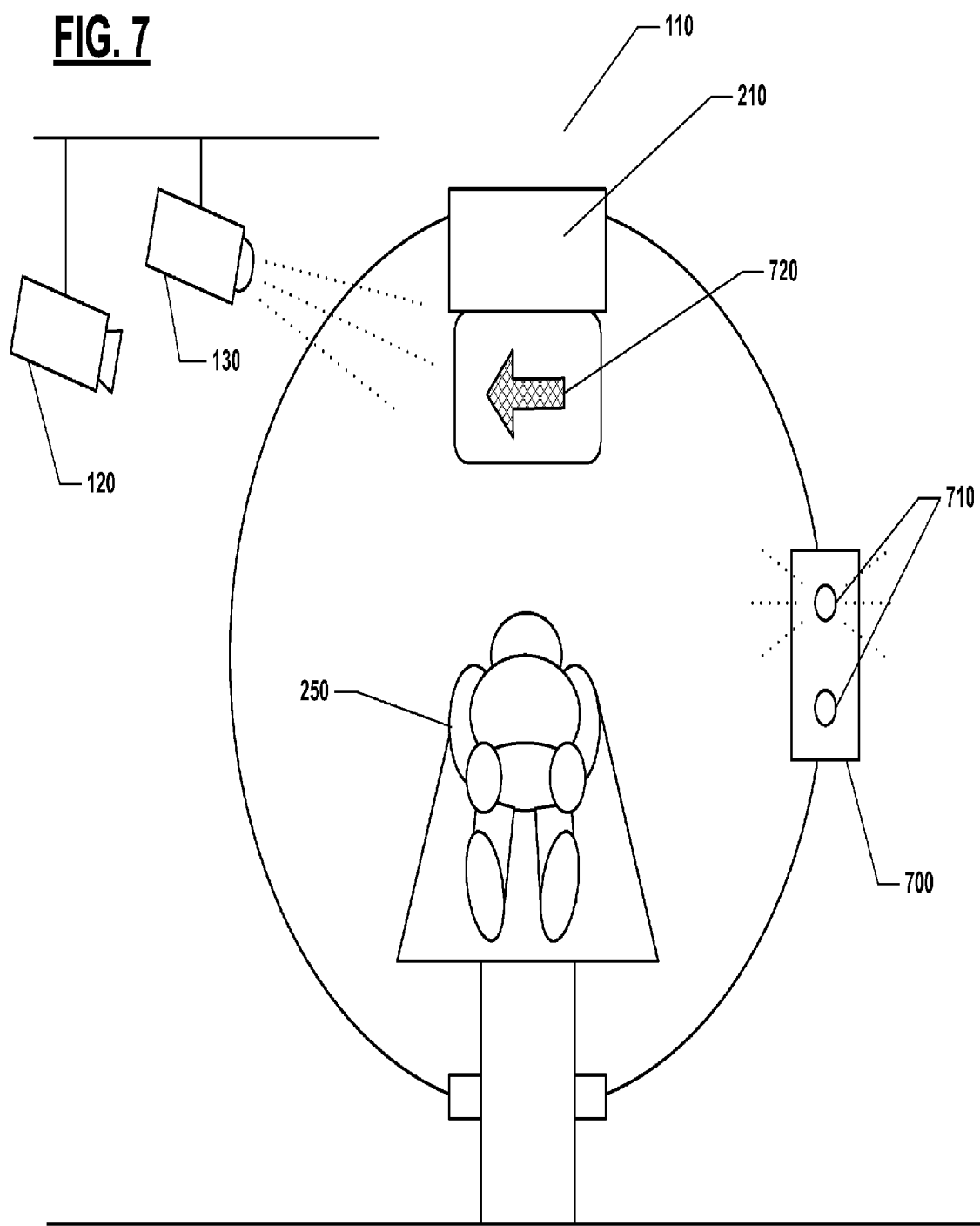
FIG. 7 is an illustration of an exemplary treatment environment including alert devices and visual indicators in accordance with an embodiment of the invention.

Referring to FIG. 7, an arrow 720 is projected onto the radiotherapy equipment 110 by the projection device 130. The arrow 720 indicates that the LINAC head 210 should be moved in the direction the arrow 720 is pointing. In some embodiments, the arrow 720 may be a particular color to indicate how close a collision is to occurring. An operator 180 viewing the treatment delivery on the output display 170 can then rotate the head 210 in that direction until the head 720 is positioned correctly. As the head 210 is being moved into position, the arrow 720 may change colors to (e.g., from red to yellow to green) to show that the LINAC head 210 is being moved away from a potential collision. Alternatively or in addition, the arrow 720 may change into different symbols as the head 210 is rotated, and may change into a verifying indicator, such as a checkmark, when the head 210 has obtained sufficient clearance. The arrow 720 or other symbol may be projected onto the patient 250, or other surface that is in danger of collision. In other embodiments, an arrow 720 (or other symbol) projected on the radiotherapy equipment 110 indicates that the patient 250 should be moved in the direction of the arrow 720 to avoid a collision with the moving equipment 110. An operator 180 viewing the treatment delivery on the output display 170 can then manually stop or make changes to the delivery, or take any other appropriate action, such as moving the patient 250 as indicated.

In other embodiments, warning lights may be arranged on various protrusions or other portions of the radiotherapy equipment 110. For example, a moving component 700 of the equipment 110 may have one or more multicolored LED lights 710 disposed on its surface. The lights 710 shine green when operation of the equipment 110 is proceeding without issue, but when the controller 150 detects that the protrusion 700 is starting to encroach on the patient 250 or another object, the lights 710 change to yellow or amber. If the distance between the protrusion 700 and the patient 250 or other object continues to close, and the controller 150 believes a collision is imminent, the lights 710 change to red (or flashing red). Again, as described above, an operator 180 viewing the treatment delivery on the output display 170 would then be able to manually stop or make changes to the operation of the equipment 110.

In certain embodiments, the system includes an auditory signal device responsive to the controller 150. The signal varies as the controller 150 detects that the proximity between monitored objects in the treatment environment 105 is increasing or decreasing. For example, the auditory signal may be a repeating tone that increases in frequency or pitch as two objects near a state of collision. The signal device may also be used with data provided by other sensors, such as an ultrasound touchgard, as disclosed in U.S. Patent Publication 2012/0039152 A1, entitled "Sensor Array," and filed Aug. 11, 2010, the entirety of which is hereby incorporated by reference.

The controller 150 may be implemented as software executing on a computer, or as integrated circuitry (e.g., an FPGA or other microchip). One skilled in the art will recognize the various forms in which the controller 150 may be implemented. If implemented as software, the controller may execute on a system capable of running a commercial operating system such as the Microsoft Windows® operating systems, the Apple OS X® operating systems, the Apple iOS® platform, the Google Android™ platform, the Linux® operating system and other variants of UNIX® operating systems, and the like.

The controller 150 may also be implemented on such hardware as a smart or dumb terminal, network computer, wireless device, smartphone, laptop, tablet computer, information appliance, workstation, minicomputer, mainframe computer, or other computing device that is operated as a general purpose computer or a special purpose hardware device. The controller 150 may be implemented on a general purpose computing device in the form of a computer including a processing unit, a system memory, and a system bus that couples various system components including the system memory to the processing unit.

The controller 150 may be implemented in various forms, for example, it may be in the form of a standalone application, implemented in a multi-platform language/framework such as Java, .Net, Objective C, or in native processor executable code. Any suitable programming language may be used in accordance with the various embodiments of the invention. Illustratively, a programming language used may include assembly language, Ada, APL, Basic, C, C++, C#, Objective C, COBOL, dBase, Forth, FORTRAN, Java, Modula-2, Pascal, Prolog, REXX, and/or JavaScript, for example. Further, it is not necessary that a single type of instruction or programming language be utilized in conjunction with the operation of the system and method of the invention. Rather, any number of different programming languages may be utilized as is necessary or desirable.

The invention may also be practiced in distributed computing environments where tasks are performed by remote processing devices that are linked through a communications network. In a distributed computing environment, program modules may be located in both local and remote computer storage media including memory storage devices.

The controller 150 may be implemented on a system including a variety of computer readable media that can form part of the system memory and be read by the processing unit. By way of example, and not limitation, computer readable media may comprise computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data.

At a minimum, the memory includes at least one set of instructions that is either permanently or temporarily stored. The processor executes the instructions that are stored in order to process data. The set of instructions may include various instructions that perform a particular task or tasks. Such a set of instructions for performing a particular task may be characterized as a program, software program, software, engine, module, component, mechanism, or tool.

The computing environment may also include other removable/non-removable, volatile/nonvolatile computer storage media. For example, a hard disk drive may read or write to non-removable, nonvolatile magnetic media. A magnetic disk drive may read from or writes to a removable, nonvolatile magnetic disk, and an optical disk drive may read from or write to a removable, nonvolatile optical disk such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or non-removable memory interface.

The processing unit that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID integrated circuits, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner. Additionally, it is appreciated that each of the processor and/or memory may be composed of different physical pieces of equipment.

A user may enter commands and information into the computer through a user interface that includes input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit through a user input interface that is coupled to the system bus, but may be connected by other interface and bus structures, such as a parallel port, game port or a universal serial bus (USB).

One or more monitors or display devices may also be connected to the system bus via an interface. In addition to display devices, computers may also include other peripheral output devices, which may be connected through an output peripheral interface. The computers implementing the invention may operate in a networked environment using logical connections to one or more remote computers, the remote computers typically including many or all of the elements described above.

Although internal components of the computer are not shown, those of ordinary skill in the art will appreciate that such components and the interconnections are well known. Accordingly, additional details concerning the internal construction of the computer need not be disclosed in connection with the present invention.

The foregoing discussion discloses and describes merely exemplary embodiments of the present invention. As will be understood by those skilled in the art, the present invention may be embodied in other specific forms without departing from the spirit or essential characteristics thereof. Various steps as described in the figures and specification may be added or removed from the processes described herein, and the steps described may be performed in an alternative order, consistent with the spirit of the invention. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology.

What is claimed is:

1. A system for controlling radiotherapy equipment in a treatment environment, the system comprising:
    a connection to one or more image capture devices for obtaining images of objects located within the treatment environment; and
    a controller for:
        receiving, from the one or more image capture devices, data indicating a position of one or more objects in the treatment environment;
        defining, based at least in part on the position data and a range of movement of the one or more of the objects estimated before delivering a radiotherapy treatment, an exclusionary zone from which the radiotherapy equipment is excluded, the exclusionary zone comprising a buffer at least partially surrounding one or more of the objects, wherein defining the exclusionary zone further includes determining a surface normal distance for the buffer such that the exclusionary zone is sufficient to accommodate the estimated range of movement of the one or more of the objects during treatment;
        designing a radiotherapy treatment plan before delivering the radiotherapy treatment, wherein the radiotherapy treatment plan excludes the equipment from entering into the exclusionary zone; and
        directing the radiotherapy equipment to deliver the radiotherapy treatment according to the radiotherapy treatment plan.

2. The system of claim 1, wherein the controller is further for:
    receiving, from the one or more image capture devices, data indicating a new position of a moved one of the objects, the new position comprising at least a portion of the moved object outside of the exclusionary zone previously containing the moved object; and in response to the new position data, redefining the exclusionary zone previously containing the moved object such that the redefined zone comprises a buffer surrounding the moved object.

3. The system of claim 2, wherein the controller is further for:
determining that the redefined exclusionary zone at least partially overlaps with a different one of the exclusionary zones;
determining whether a combination between the redefined zone and the different zone is permissible; and
combining the redefined zone and the different zone to form a single continuous exclusionary zone.

4. The system of claim 3, wherein the combination determination is based at least in part on a visual indicator disposed on an object at least partially contained within one or more of the zones to be combined.

5. The system of claim 1, wherein the controller is further for:
defining a first exclusionary zone having a first buffer surrounding one or more substantially motionless objects in the treatment environment; and
defining a second exclusionary zone having a second buffer surrounding one or more moving objects in the treatment environment, the second buffer having a surface normal distance greater than the first buffer.

6. The system of claim 1, wherein directing the radiotherapy equipment comprises at least one of changing a speed of the radiotherapy equipment, changing a direction of the radiotherapy equipment, and terminating movement of the radiotherapy equipment.

7. The system of claim 1, wherein the controller receives the position data from a plurality of image capture devices, wherein the controller is further for determining the position of each image capture device based at least in part on a visual indicator in a field of view of the image capture device.

8. The system of claim 1, further including a projection device for projection onto a surface in the treatment environment, at least one of a visual indicator of an action to be taken with respect to an object in the treatment environment and a visual indicator of a warning that a collision is likely to occur.

9. The system of claim 1, further including one or more colored lights on a portion of the radiotherapy equipment, wherein the controller is further for changing a state of the one or more colored lights based on a proximity of the portion of the radiotherapy equipment to another object in the treatment environment.

10. A method for controlling radiotherapy equipment in a treatment environment, the method comprising:
receiving, from one or more image capture devices, data indicating a position of one or more objects in the treatment environment;
defining, based at least in part on the position data and a range of movement of the one or more of the objects estimated before delivering a radiotherapy treatment, an exclusionary zone from which the radiotherapy equipment is excluded, the exclusionary zone comprising a buffer at least partially surrounding one or more of the objects, wherein defining the exclusionary zone further includes determining a surface normal distance for the buffer such that the exclusionary zone is sufficient to accommodate the estimated range of movement of the one or more of the objects during treatment;
designing a radiotherapy treatment plan before delivering the radiotherapy treatment, wherein the radiotherapy treatment plan excludes the equipment from entering into the exclusionary zone; and
directing the radiotherapy equipment to deliver the radiotherapy treatment according to the radiotherapy treatment plan.

11. The method of claim 10, further comprising:
receiving, from the one or more image capture devices, data indicating a new position of a moved one of the objects, the new position comprising at least a portion of the moved object outside of the exclusionary zone previously containing the moved object; and
in response to the new position data, redefining the exclusionary zone previously containing the moved object such that the redefined zone comprises a buffer surrounding the moved object.

12. The method of claim 11, further comprising:
determining that the redefined exclusionary zone at least partially overlaps with a different exclusionary zone; and
combining the redefined zone and the different zone to form a single continuous exclusionary zone.

13. The method of claim 12, wherein the combination determination is based at least in part on a visual indicator disposed on an object at least partially contained within one or more of the zones to be combined.

14. The method of claim 10, further comprising:
determining that a boundary of the exclusionary zone is within a threshold distance of a boundary of a second exclusionary zones; and
combining the zone and the second zone to form a single continuous exclusionary zone.

15. The method of claim 10, further comprising:
determining, based on object motion information, that an object in the exclusionary zone has increased in speed;
redefining the exclusionary zone by extending its buffer.

16. The method of claim 10, wherein the receiving the position data comprises receiving the position data from a plurality of image capture devices, wherein the controller is further for determining the position of each image capture device based at least in part on a visual indicator in a field of view of the image capture device.

17. A system for controlling radiotherapy equipment in a treatment environment the system comprising:
a connection to one or more image capture devices;
a controller for:
receiving, from the one or more image capture devices, data indicating a position of one or more objects in the treatment environment;
defining, based at least in part on the position data and a range of movement of the one or more of the objects estimated before delivering a radiotherapy treatment, an exclusionary zone from which the radiotherapy equipment is excluded;
detecting, based on the position data, that at least a portion of the one or more of the objects has moved outside the exclusionary zone;
redefining, based at least in part on the position data, the exclusionary zone by extending or contracting its buffer to enclose the portion inside the exclusionary zone; and
directing the radiotherapy equipment to deliver the radiotherapy treatment such that the equipment does not enter into the exclusionary zone.

18. The system of claim 17, wherein the controller is further for determining object motion information based on position data received during the radiotherapy treatment, and redefining the exclusionary zone based at least in part on the object motion information.

19. The system of claim 18, wherein the controller is further for determining, based on the object motion information, that an object in the exclusionary zone has increased in speed, and redefining the exclusionary zone by extending its buffer.

20. A method for controlling radiotherapy equipment in a treatment environment, the method comprising:
- receiving, from one or more image capture devices, data indicating a position of one or more objects in the treatment environment;
- defining, based at least in part on the position data and a range of movement of the one or more of the objects estimated before delivering a radiotherapy treatment, an exclusionary zone from which the radiotherapy equipment is excluded;
- detecting, based on the position data, that at least a portion of the one or more of the objects has moved outside the exclusionary zone;
- redefining, based at least in part on the position data, the exclusionary zone by changing its buffer to enclose the portion inside the exclusionary zone; and
- directing the radiotherapy equipment to deliver the radiotherapy treatment such that the equipment does not enter into the exclusionary zone.

* * * * *